United States Patent
Marseille et al.

(10) Patent No.: US 12,280,192 B2
(45) Date of Patent: Apr. 22, 2025

(54) GAS EXCHANGE UNIT

(71) Applicant: Hemovent GmbH, Aachen (DE)

(72) Inventors: Oliver Marseille, Aachen (DE); Andreas Nobis, Würselen (DE); Stefan Nötzel, Aachen (DE); Felix Hesselmann, Aachen (DE)

(73) Assignee: Hemovent GmbH, Aachen (DE)

( * ) Notice: Subject to any disclaimer, the term of this patent is extended or adjusted under 35 U.S.C. 154(b) by 420 days.

(21) Appl. No.: 16/647,930

(22) PCT Filed: Sep. 20, 2018

(86) PCT No.: PCT/EP2018/075541
§ 371 (c)(1),
(2) Date: Mar. 17, 2020

(87) PCT Pub. No.: WO2019/057858
PCT Pub. Date: Mar. 28, 2019

(65) Prior Publication Data
US 2020/0276375 A1    Sep. 3, 2020

(30) Foreign Application Priority Data

Sep. 20, 2017  (DE) .................... 10 2017 008 781.4
Mar. 29, 2018  (LU) ...................................... 100759

(51) Int. Cl.
*A61M 1/16*    (2006.01)

(52) U.S. Cl.
CPC ....... *A61M 1/1698* (2013.01); *A61M 2206/20* (2013.01); *A61M 2207/00* (2013.01); *B01D 2313/08* (2013.01)

(58) Field of Classification Search
CPC ............ A61M 1/1698; A61M 2206/20; A61M 2207/00; A61M 2206/12; B01D 63/02; B01D 2313/08; B01D 2313/20; B01D 63/026
See application file for complete search history.

(56) References Cited

U.S. PATENT DOCUMENTS

| | | | |
|---|---|---|---|
| 2,659,368 | A | 11/1953 | Gibbon, Jr. et al. |
| 3,639,084 | A | 2/1972 | Goldhaber et al. |
| 3,838,946 | A | 10/1974 | Schall |
| 3,842,440 | A | 10/1974 | Karlson |
| 3,916,449 | A | 11/1975 | Davis |
| 3,919,722 | A | 11/1975 | Harmison |
| 4,094,792 | A | 6/1978 | Bentley |
| 4,116,589 | A | 9/1978 | Rishton |

(Continued)

FOREIGN PATENT DOCUMENTS

| | | |
|---|---|---|
| CA | 2679428 A1 | 9/2008 |
| CN | 1528472 A | 9/2004 |

(Continued)

OTHER PUBLICATIONS

International preliminary report on patentability of PCT/DE2011/000009, Jul. 2012.

(Continued)

*Primary Examiner* — Pranav N Patel
(74) *Attorney, Agent, or Firm* — Michael J. Brown

(57) ABSTRACT

Gas exchange unit comprising an inlet that is acentrically slanted, and a method for producing a gas exchange unit.

22 Claims, 12 Drawing Sheets

(56) References Cited

U.S. PATENT DOCUMENTS

| | | | |
|---|---|---|---|
| 4,182,653 A | 1/1980 | Bellhouse | |
| 4,497,104 A * | 2/1985 | Fowles | B29C 65/521 |
| | | | 264/510 |
| 5,084,244 A | 1/1992 | Muramoto | |
| 5,116,308 A * | 5/1992 | Hagiwara | A61M 60/837 |
| | | | 422/46 |
| 5,230,862 A | 7/1993 | Berry et al. | |
| 5,232,434 A | 8/1993 | Inagaki et al. | |
| 5,269,811 A | 12/1993 | Hayes et al. | |
| 5,300,111 A | 4/1994 | Panton et al. | |
| 5,314,469 A | 5/1994 | Gao | |
| 5,651,765 A | 7/1997 | Haworth et al. | |
| 5,725,763 A * | 3/1998 | Bonhomme | F16K 7/20 |
| | | | 210/406 |
| 5,751,125 A | 5/1998 | Weiss | |
| 5,782,791 A * | 7/1998 | Peterson | B01D 29/111 |
| | | | 210/493.1 |
| 5,964,725 A | 10/1999 | Sato et al. | |
| 5,965,433 A | 10/1999 | Gardetto et al. | |
| 6,117,390 A * | 9/2000 | Corey, Jr. | A61M 60/237 |
| | | | 422/44 |
| 6,264,601 B1 | 7/2001 | Jassawalla et al. | |
| 6,312,647 B1 | 11/2001 | Spears | |
| 6,454,999 B1 | 9/2002 | Farhangnia et al. | |
| 6,998,093 B1 | 2/2006 | McIntosh et al. | |
| 7,981,280 B2 | 7/2011 | Carr et al. | |
| 8,038,640 B2 | 10/2011 | Orr | |
| 8,882,695 B2 | 11/2014 | Marseille | |
| 9,974,897 B2 | 5/2018 | Marseille | |
| 2001/0003802 A1 | 6/2001 | Vitale | |
| 2002/0057989 A1 | 5/2002 | Afzal et al. | |
| 2002/0143397 A1 | 10/2002 | Von Segesser | |
| 2004/0009097 A1* | 1/2004 | Stringer | F04D 9/006 |
| | | | 604/6.11 |
| 2004/0015042 A1 | 1/2004 | Vincent et al. | |
| 2004/0050789 A1 | 3/2004 | Ash | |
| 2007/0158247 A1 | 7/2007 | Carr et al. | |
| 2008/0234623 A1 | 9/2008 | Strauss et al. | |
| 2009/0137939 A1 | 5/2009 | Maianti et al. | |
| 2009/0210162 A1 | 8/2009 | Kristiansen et al. | |
| 2010/0106072 A1 | 4/2010 | Kashefi-Khorasani et al. | |
| 2010/0211092 A1 | 8/2010 | Forsell | |
| 2010/0234941 A1 | 9/2010 | Finocchiaro et al. | |
| 2013/0004369 A1 | 1/2013 | Marseille | |
| 2013/0037485 A1 | 2/2013 | Wilt et al. | |
| 2013/0199639 A1* | 8/2013 | Hartnett | F16K 1/12 |
| | | | 137/565.11 |
| 2014/0030146 A1 | 1/2014 | Takeuchi | |
| 2014/0227134 A1 | 8/2014 | Joost et al. | |
| 2015/0129493 A1 | 5/2015 | Federspiel et al. | |
| 2016/0051740 A1 | 2/2016 | Wegener et al. | |
| 2016/0095969 A1 | 4/2016 | Maurer et al. | |
| 2016/0296685 A1 | 10/2016 | Wu et al. | |
| 2017/0258978 A1 | 9/2017 | Bartlett et al. | |
| 2018/0078695 A1* | 3/2018 | Plott | A61M 1/1698 |
| 2018/0117231 A1* | 5/2018 | Matheis | B01D 63/043 |
| 2018/0147339 A1 | 5/2018 | Marseille | |
| 2019/0160217 A1 | 5/2019 | Marseille et al. | |
| 2020/0038564 A1 | 2/2020 | Hutzenlaub | |

FOREIGN PATENT DOCUMENTS

| | | |
|---|---|---|
| CN | 103491993 A | 1/2014 |
| DE | 2737920 A1 | 3/1979 |
| DE | 3342534 A1 | 10/1984 |
| DE | 3876169 T2 | 5/1993 |
| DE | 19532365 A1 | 3/1997 |
| DE | 69422997 T2 | 10/2000 |
| DE | 60031706 T2 | 9/2007 |
| DE | 69933314 T2 | 9/2007 |
| DE | 102007010112 A1 | 9/2008 |
| DE | 102010004600 A1 | 7/2011 |
| DE | 102011052188 A1 | 1/2013 |
| DE | 102011054768 A1 | 4/2013 |
| DE | 102017000843 A1 | 8/2018 |
| EP | 0378168 A2 | 7/1990 |
| EP | 0621047 A2 | 10/1994 |
| EP | 1534360 B1 | 6/2006 |
| EP | 2517739 A2 | 10/2012 |
| EP | 2517739 B1 | 12/2013 |
| EP | 2125069 B1 | 6/2014 |
| EP | 2523702 B1 | 11/2014 |
| EP | 3090768 A1 | 11/2016 |
| EP | 3520833 A1 | 8/2019 |
| FR | 2400935 A1 | 3/1979 |
| GB | 2003052 A | 3/1979 |
| GB | 2533027 A | 6/2016 |
| JP | S5012897 A | 2/1975 |
| JP | S58500793 A | 5/1983 |
| JP | S61143075 A | 6/1986 |
| JP | H0347270 A | 2/1991 |
| JP | H04193178 A | 7/1992 |
| JP | H04504673 A | 8/1992 |
| JP | H0526169 A | 2/1993 |
| JP | 2001079083 A | 3/2001 |
| JP | 2003524454 A | 8/2003 |
| JP | 2004510521 A | 4/2004 |
| JP | 2004154425 A | 6/2004 |
| JP | 2010035869 A | 2/2010 |
| JP | 2010518995 A | 6/2010 |
| JP | 2010213851 A | 9/2010 |
| JP | 2014151115 A | 8/2014 |
| JP | 2014183945 A | 10/2014 |
| JP | 2019517375 A | 6/2019 |
| WO | WO-9511709 A2 | 5/1995 |
| WO | WO-9952621 A1 | 10/1999 |
| WO | WO-0230267 A2 | 4/2002 |
| WO | WO-0230267 A3 | 11/2002 |
| WO | WO-2004043517 A2 | 5/2004 |
| WO | WO-2004098678 A1 | 11/2004 |
| WO | WO-2005028002 A1 | 3/2005 |
| WO | WO-2008104353 A1 | 9/2008 |
| WO | WO-2009024308 A1 | 2/2009 |
| WO | WO-2009110652 A1 | 9/2009 |
| WO | WO-2011085714 A1 | 7/2011 |
| WO | WO-2014183852 A1 | 11/2014 |
| WO | WO-2016030917 A2 | 3/2016 |
| WO | WO-2016110613 A1 | 7/2016 |
| WO | WO-2016177476 A1 | 11/2016 |
| WO | WO-2017211460 A1 | 12/2017 |
| WO | WO-2018057892 A1 | 3/2018 |
| WO | WO-2018141316 A1 | 8/2018 |
| WO | WO-2019057858 A1 | 3/2019 |

OTHER PUBLICATIONS

International Search Report for PCT/DE2017/000376 on Aug. 9, 2018.
International search report of PCT/DE2011/000009, date of mailing May 31, 2011.
Notice of allowance dated Jul. 3, 2014 for U.S. Appl. No. 13/521,857.
Notice of Allowance dated Oct. 26, 2017 for U.S. Appl. No. 14/506,329.
Office Action dated Feb. 12, 2014 for U.S. Appl. No. 13/521,857.
Office Action dated Apr. 20, 2017 for U.S. Appl. No. 14/506,329.
Office Action dated Jul. 30, 2013 for U.S. Appl. No. 13/521,857.
Office Action dated Dec. 19, 2012 for U.S. Appl. No. 13/521,857.
PCT/EP2017-000685 Search Report & Written Opinion dated Dec. 14, 2017.
PCT/EP2018-075541 Search Report & Written Opinion dated Mar. 28, 2019.
U.S. Appl. No. 14/506,329 Notice of Allowance dated Apr. 24, 2018.
U.S. Appl. No. 14/506,329 Notice of Allowance dated Mar. 15, 2018.
U.S. Appl. No. 14/506,629 Office Action dated Jun. 17, 2016.
CN 201780045093.1 Office Action dated Jan. 28, 2021.
JP2019-517139 Translation of Office Action dated Jan. 27, 2021.
U.S. Appl. No. 15/881,292 Office Action dated Jul. 24, 2020.
Co-pending U.S. Appl. No. 17/827,516, inventor Marseille; Oliver, filed May 27, 2022.

(56) References Cited

OTHER PUBLICATIONS

Co-pending U.S. Appl. No. 17/504,171, inventor Marseille; Oliver, filed Oct. 18, 2021.
U.S. Appl. No. 15/881,292 Notice of Allowance dated Jul. 21, 2021.
U.S. Appl. No. 15/881,292 Office Action dated Feb. 11, 2021.
Co-pending U.S. Appl. No. 18/094,198, inventor Marseille; Oliver, filed Jan. 6, 2023.
U.S. Appl. No. 16/308,505 Office Action dated Mar. 16, 2023.
U.S. Appl. No. 14/506,329 Office Action dated Jun. 17, 2016.
U.S. Appl. No. 16/308,505 Office Action dated Dec. 27, 2023.

* cited by examiner

GAS EXCHANGE UNIT

The invention relates to a gas exchange unit and a method for producing a gas exchange unit.

BACKGROUND OF THE INVENTION

In patients with life-threatening lung conditions lung function can be maintained with an artificial lung (oxygenator or gas exchange unit) until the lung has recovered and natural lung function is reinstated. Extracorporeal circulation extracts the blood of the patient and returns the same following treatment in the oxygenator for this.

Most known oxygenators were developed as part of developing the heart-lung machine for use during heart surgery measures of a few hours and are mostly not optimised for long-term application. The application period that is part of respiratory support is however often clearly longer and can last a few weeks. During a long application period of a known oxygenator haemolysis and thrombus formation can for example occur due to a suboptimal flow path with high flow resistances and poorly flushed areas. The exchange capacity of such oxygenators also drops, so that these must be replaced during treatment, wherein complications and also blood loss or severe blood thinning may occur.

Conventional oxygenators for example consist of stacked hollow fibre mats arranged reciprocally at right angles to each other. In the edge area the mats are embedded four times with a casting compound by means of a spinning or centrifugal method, which results in a square cross-section surface, through which the blood flows. In order to distribute the blood across the fibre surface as evenly as possible perforated distribution plates are used with conventional oxygenators, which are installed in the inlet area and outlet area of the oxygenator. Such an oxygenator is for example from WO 2017/211460 A1.

SUMMARY OF THE INVENTION

It is the task of the present invention to improve the flow guidance in an oxygenator, so that the requirements of medium- to long-term respiratory support can be satisfied in a simple way.

The task is solved according to the invention by the characteristics of the independent claims. Further developments of the invention result from the subclaims.

According to the invention a gas exchange unit comprising hollow fibre mats is provided, wherein the gas exchange unit comprises an inlet that is positioned diagonally acentric. To distribute blood flow through the gas exchange unit as homogeneously as possible across the circular fibre surface, and here in particular to ensure adequate flow in the edge area, blood it rotated by means of the acentric diagonal inlet. The hollow fibre mats have a circular cross-section surface. The inlet of the gas exchange unit is arranged acentric in relation to the fibre layers of the hollow fibre mats in a further development.

As described below the measures according to the invention form a gas exchange unit where the distribution plates are omitted and fluid (in particular blood) flows evenly across the fibre surface formed from the hollow fibre mats with other means or measures. The gas exchange unit according to the invention has a longer application period or service life than known oxygenators. The probability of blood damage is also low with the gas exchange unit stated.

The hollow fibre mats of the gas exchange unit are formed from hollow fibres. The gas exchange unit can comprise one or more hollow fibre mats. The fibre orientation of a fibre mat can be arranged at an angle to the fibre orientation of a further fibre mat. Crossing the fibre mats can improve the gas exchange characteristics as well as blood guidance.

The gas exchange unit is also described as an oxygenator. An oxygenator is an apparatus where blood can be enriched with oxygen and carbon dioxide removed from the blood. The lung can thus be replaced or supported by means of the oxygenator in the short term as well as for longer periods.

The gas exchange unit envisages in one further development that the inlet is arranged on the facing side on a casing of the gas exchange unit. The arrangement of an inlet on the facing side of the gas exchange unit allows a homogeneous flow through the hollow fibre mats. The casing of the gas exchange unit has an inlet casing.

According to a further development of the gas exchange unit it is envisaged that the inlet is connected with the inlet casing, the surface of which has structures. Suitable structures on the inner, blood conveying surface of the inlet casing further distribute the flow as homogeneously as possible. The inlet is positioned diagonally here when an angle between a central axis of the inlet and a level that includes the inlet casing is larger than 0° and/or smaller than 90°.

In a further development of the gas exchange unit it is envisaged that the structures are vane-shaped, bridge-shaped or arranged as cross members on the surface of the inlet casing. The structures, which are vane-shaped, bridge-shaped or arranged in as cross members, can distribute the flow across or the supply of the fibre surfaces in the gas exchange unit evenly. The flow is consistent in the inner as well as the outer area of the hollow fibre mats.

According to a further development of the gas exchange unit it is envisaged that the inlet has a cross-section surface that widens continuously in flow direction, so that the flow speed is reduced slowly and not suddenly. The ratio of dD/2dL<1 between diameter (dD) and run length (dL) of the inlet is advantageous. (In other words, the ratio between the radius of the inlet and the run length is less than 1). This ratio changes across the run length. It can also change gradually in the area of the inlet.

According to a further development a diameter widening of the inlet is less than 45° across the run length.

According to a further development of the gas exchange unit it is envisaged that the cross-section surface of the inlet widens asymmetrically. The widening can be symmetrical in order to guide the flow in a targeted way and thus distribute it homogeneously.

In a further development of the gas exchange unit it is envisaged that the inlet has a cross-section surface that is variable across the length of the inlet.

In a further development of the gas exchange unit it is envisaged that the gas exchange unit has an outlet, the cross-section surface of which reduces in flow direction. The fluid, in particular blood, is accelerated through a continuous cross-section surface reduction. A ratio of less than 1 between the diameter widening (dD) and the run length (dL) is advantageous: dD/dL<1 or dD/2dL.

According to another further development of the gas exchange unit it is envisaged that the gas exchange unit has an outlet comprising a deflection. To realise the most compact gas exchange unit possible the flow of the fluid, in particular blood, is deflected at an angle on the outlet side. The deflection angle is approximately 90° or between 70° and 90°. Secondary turbulence or flow separations of the fluid, in particular of the blood, may occur with such deflections. With a continuous reduction in the cross-section surface of the outlet the fluid is however accelerated, so that the formation of secondary turbulence or flow separations are counteracted or are almost prevented.

According to an independent idea of the invention the gas exchange unit or the oxygenator comprises a ventilation device, in particular arranged substantially centrally. If air is taken in, this is collected in the middle of the rotating flow due to the inlet geometry, formed of inlet and inlet casing, in particular in a cavity of the gas exchange unit. Air is aspirated by the ventilation device. The ventilation device is also an outlet for air bubbles that may collect at these points during operation. The ventilation devices can also be used for blood sampling whilst treating a patient.

To prevent the formation of blood coagulum (thrombi) it must be possible to flush all areas of the ventilation device or it must be prevented that blood lingers.

The ventilation device can be designed in such a way that it can optionally be realised in a first operating condition, under which a flushing of the ventilation device can be realised or it can be transferred into a second operating condition, in which a ventilation of the cavity of the gas exchange unit can be realised. Two technical functions can therefore advantageously be realised by means of the ventilation device, namely ventilation of the cavity and the flushing, and thus cleaning of the ventilation device. The ventilation device is preferably flushed after a ventilation process. It can thus be prevented that possible blood residues that may also flow out during a ventilation process remain in the ventilation device. Alternatively the ventilation device can optionally be transferred into the first operating condition, where no ventilation of the cavity of the gas exchange unit takes place, or into the second operating condition, where a ventilation of the cavity of the gas exchange unit takes place. With this design only one technical function, namely the ventilation of the cavity, can be realised with the ventilation device.

The gas exchange unit can have an underpressure source that can be fluid-connected with the ventilation device. It can be ensured in a simple way by applying underpressure in the ventilation device by means of the underpressure source that the air located in the cavity can be vented from the same.

In a further development of the gas exchange unit it is envisaged that the ventilation device comprises a flexible membrane. The central area of the inlet is made of a flexible material, so that the same can be turned inside out for ventilation purposes, so that a larger volume results on the blood side for collecting the air bubbles.

The gas exchange unit can have an adjustment element that serves for transferring the ventilation device into the first operating condition or into the second operating condition. Depending on the individual case the adjustment element can be designed differently, as is explained in more detail below.

The ventilation device can have a closure piston that is transferred into a first position for realising the first operating condition, or into a second position for realising the second operating condition. The closure piston can be moved linearly and/or rotatably mounted here, so that the same can be transferred from the first position into the second position or vice versa. In particular the closure piston can be mounted to rotate around its longitudinal axis. Alternatively or in addition the closure piston can be designed in such a way that a piston section is moved relative to another piston section for transferring the closure piston from the first position into the second position.

The closure piston can have a fluid line that is not fluid-connected with the cavity in the first position of the closure piston, and is in fluid-connection with the cavity in the second position of the closure piston. In addition the fluid line can be in fluid-connection with a supply line for supplying a flushing agent in the first position of the closure piston, and is not in fluid-connection with the supply line in the second position of the closure piston. In the second position the air located in the cavity can be vented from the cavity via the fluid line. With this design the closure piston can be rotatably mounted and the adjustment element can be designed in such a way that the closure piston is turned upon actuating the adjustment element. The adjustment element can preferably be connected with the closure piston in a torque-roof way.

With a further development a sealing ring of the ventilation device can be fitted to the closure piston. In addition the ventilation device can have a return member that is operatively connected with the closure piston in such a way that the return member pushes the closure piston out of the second position into the first position. The closure piston can be mounted in a linearly moveable way with this design. The return member can be a spring, in particular a pressure spring. A force, in particular a linear force, is applied to the closure piston by means of the adjustment element for transferring the closure piston from the first position into the second position. The adjustment element can for example be a syringe.

The closure piston can have a weak point in a further development, which is designed in such a way that it projects through the closure piston in the second position of the closure element. In the first position of the closure piston the closure piston can prevent an exit of air or blood from the cavity despite the weak point. The adjustment element can be a pipette that has at least one opening in its section that projects through the closure piston. Air located in the cavity can be vented from said cavity via the opening and the adjustment element here. The weak point of the closure piston can be realised with a cut in the closure piston.

To improve the gas exchange unit further it is envisaged in one further development that the hollow fibre mats are embedded in the gas exchange unit and have slanting transition from the embedded hollow fibre mats to adjacent components. The position of the transition from free fibres to the embedded fibres (potting level) can be subject to imprecise tolerances. The slanting transition with which the neighbouring, blood carrying components are equipped results in a smooth, impact-free, and therefore blood-friendly transition even for different positions of the potting level. The measure of the slanting transitions also strongly simplifies the manufacturing process of the gas exchange unit, as the tolerances lead to a lower quality loss over a wider range during manufacture. In a further development of the gas exchange unit it is envisaged that the inlet casing has stabilisers. In order to achieve a stability increase for the inlet casing during potting the inlet casing has stabilisers. These can be designed as bridges or cross members. The inlet geometry is therefore maintained during potting, where high temperatures and/or tension can be reached, and does not change substantially due to temperature changes.

The hollow fibres of known oxygenators are normally first closed at their ends and then embedded in a polyurethane adhesive. This potting step is carried out with a spinning method to prevent adhesion of the fibres in the area that later conveys blood due to capillary effects, and to enable a defined transition between the potting mass and free fibres. The fibres are then cut open with the cured potting mass from the outside transverse to the fibre direction in order to later enable a flow through the fibres with gas. The potting step normally takes place at both ends of the fibres and two potting processes therefore result with oxygenators with fibres arranged in parallel, or four potting steps with stacked fibre mats.

According to the invention a method for producing a gas exchange unit is offered. The method comprises: insertion of the casting mass for embedding the fibre ends, wherein this insertion takes place once, and forming a cylindrical cavity in the central area of the gas exchange unit.

The gas exchange unit according to the invention is produced from stacked hollow fibre mats. The casting mass for embedding the fibre ends is introduced during a step in a centrifuge with the method for producing a gas exchange unit, so that a cylindrical cavity results in the central area of the gas exchange unit, in which the hollow fibres come into contact with a fluid, in particular blood. The cylindrical cavity results in a homogeneous flow through the fibre mats. A requirement for this is a consistent facing side flow onto the cylindrical cavity. The selected construction shape realises a gas exchange unit with which production costs are low thanks to reducing manufacturing steps, as the fibres are embedded during one working step. With gas exchange units currently available on the market, embedding the fibres takes place during two or even four time-consuming steps in a centrifuge.

All components that come into contact with blood are also added in one working step with the described method. Further gluing is not necessary.

Contrary to this the homogeneous flow through the fibre mats takes place via distribution or diffusion plates with known oxygenators, which increase the flow resistance to various different degrees in a targeted way and distribute blood flow in this way. It is a disadvantage here that additional shear stresses and irritation can damage the blood. Thrombi can also be generated in the rear areas of the distribution plates where the flow is switched off, as wake spaces can be created there. Such plates can be omitted with the measures of the invention.

BRIEF DESCRIPTION OF THE FIGURES

Further details of the invention can be found in the embodiment examples, which are described with reference to the Figures below. Shown are.

DETAILED DESCRIPTION OF THE FIGURES

Figure 1:
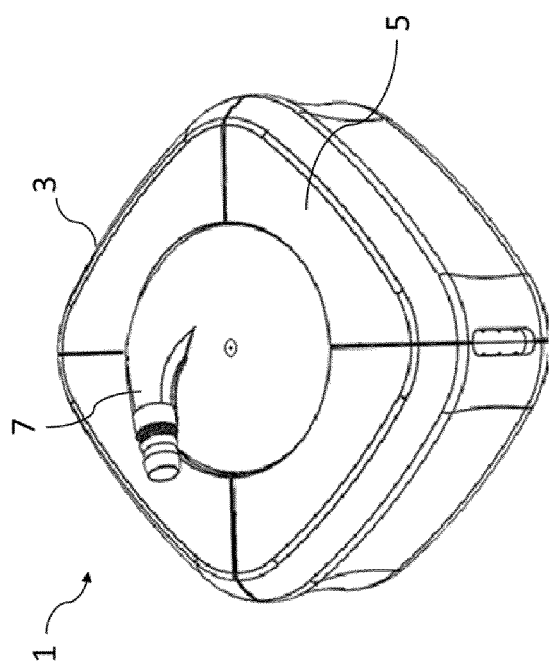
FIG. 1: an embodiment example of a gas exchange unit.

Examples of embodiments of the invention will be described below with reference to the enclosed drawings:

FIG. 1 shows an embodiment example of a gas exchange unit 1, which comprises hollow fibre mats (not shown). The gas exchange unit 1 comprises an inlet 7, arranged acentrically on an inlet casing 5. The inlet 7 is positioned diagonally to the inlet casing 5. The inlet 7 is arranged on the facing side of a casing of the gas exchange unit 1 that includes the inlet casing 5 and enables a homogeneous flow through the hollow fibre mats. The inlet casing 5 forms a facing side of the casing of the gas exchange unit 1. The inlet casing 5 is covered by a casing part 3 of the gas exchange unit 1 in its edge area (compare for example FIG. 1).

Figure 2:
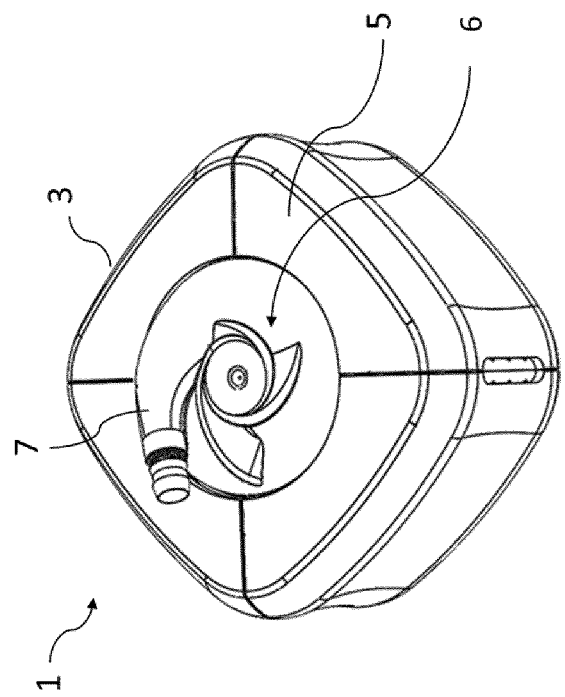
FIG. 2: a further embodiment example of a gas exchange unit.

FIG. 2 shows a further embodiment example of a gas exchange unit 1. The surface of the inlet casing 5 has structures 6 that additionally distributes the flow of blood flowing through as homogeneously as possible on the inner, blood-conveying surface of the inlet casing 5. The inlet casing 5 can optionally have the stabilisers 8 shown in FIG. 3. The stabilisers 8 can be designed as bridges or cross members. With a potting, during which high temperatures and/or tensions can be reached, the inlet geometry of the inlet casing 5 is thus maintained and does not change substantially during temperature and/or tension changes.

Figure 3:
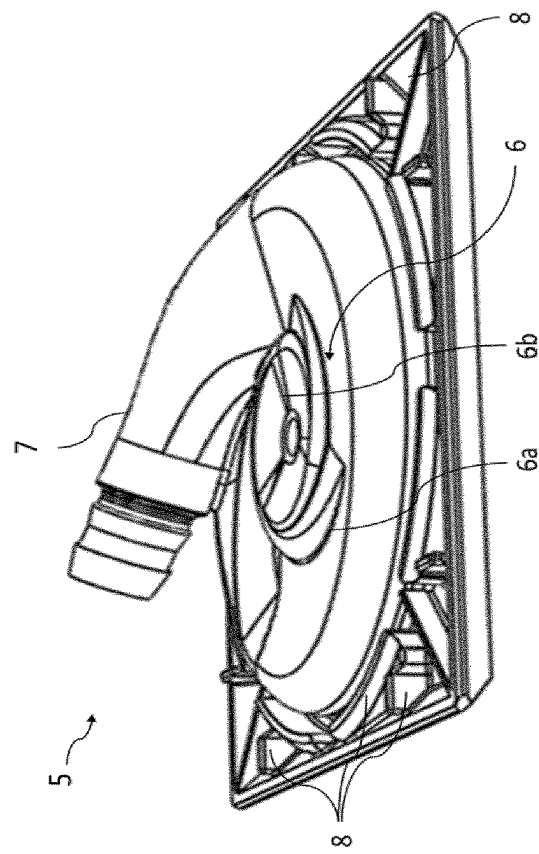
FIG. 3: the inlet casing of FIG. 2.

FIG. 3 shows the inlet casing 5 from FIG. 2. The acentric diagonal arrangement of the inlet 7 is clearly recognisable. The structures 6 that distribute the flow homogeneously in the gas exchange unit 1 are designed as vane-shaped structures 6a and as bridge-shaped structures 6b. The structures 6 can also be arranged as cross members on the surface of the inlet casing 5.

These structures 6 mean that a flow through, or a supply of the fibre surfaces of the hollow fibre mats in the gas exchange unit 1 takes place consistently in the inner, central area of the hollow fibre mats as well as in the outer area, which comprises an edge area of the hollow fibre mats.

Figure 4:
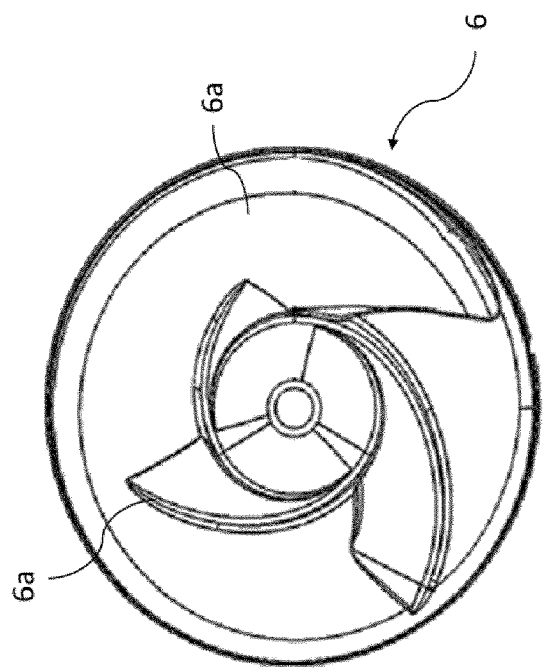
FIG. 4: an embodiment example of a surface of an inlet casing.

FIG. 4 shows an embodiment example of a structured surface of an inlet casing 5 in a top view. The different size of the vane-shaped structures 6a is recognisable. It guarantees a consistent, homogeneous flow through the gas exchange unit 1.

Figure 5:
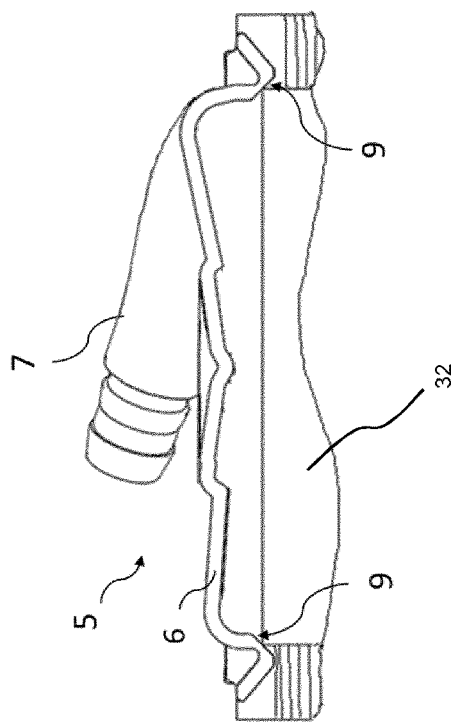
FIG. 5: a cross-section view of an inlet casing.

FIG. 5 shows a cross-section view of an inlet casing 5. The diagonal positioning of the inlet 7 as well as the acentric arrangement are also visible in this Figure. The inlet casing 5 includes the structures 6. The hollow fibre mats 32 are embedded in the gas exchange unit 1 and are in contact with the inlet casing 5. The inlet casing 5 has slanting transitions 9 in the contact area of the hollow fibre mats 32 with the inlet casing 5. The position of the respective transition 9 from the free fibres to the embedded 10 fibres (potting level) can be subject to imprecise tolerances.

The slanting transitions 9 also result in a consistent, smooth, and therefore blood-friendly transition even with different positions of the potting level.

Figure 6:
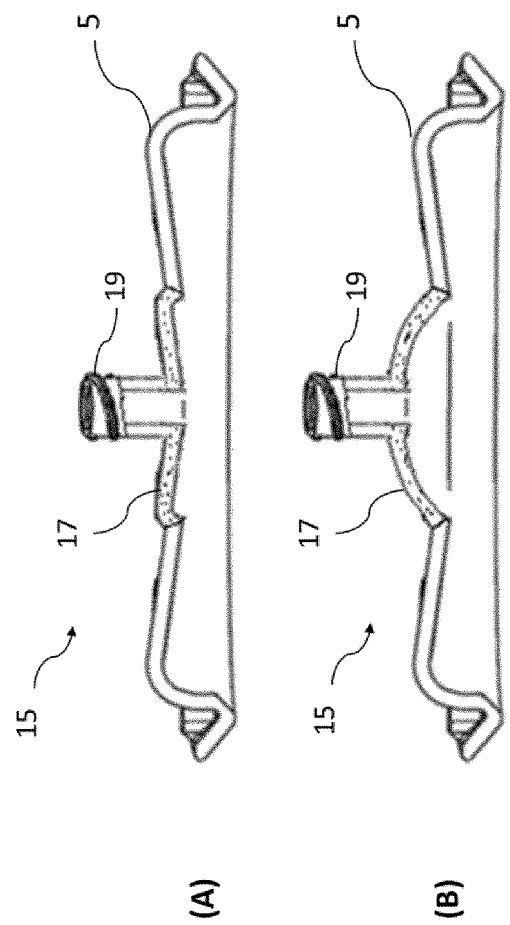
FIG. 6: an embodiment example of a ventilation device according to a first design.

FIG. 6 shows an embodiment example of a ventilation device 15. If air should be drawn in this will accumulate in the centre of the rotating flow due to the inlet geometry formed by inlet 7 and inlet casing 5. The air is aspirated by the ventilation device 15 there. The ventilation device 15 is also an outlet for air bubbles. The ventilation device 15 comprises a ventilation pipe 19.

The ventilation device 15 comprises a flexible membrane 17. Part (A) of FIG. 6 shows the membrane 17 in a condition without ventilation. During ventilation, shown in Part (B) of FIG. 7, the membrane 17 is turned inside out, so that an enlarged volume results on the blood side for collecting the air bubbles.

Figure 7:
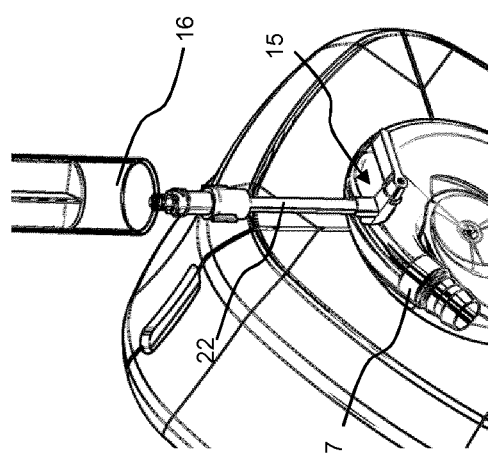
FIG. 7: a perspective illustration of a ventilation device according to a second design.

FIG. 7 shows a perspective illustration of a ventilation device 15 according to a second design. The ventilation device 15 is arranged next to the inlet 7. The ventilation device 15 is also fluid-connected with an underpressure source 16 by means of a line 22. The underpressure source 16 is designed as a syringe.

Figure 8:
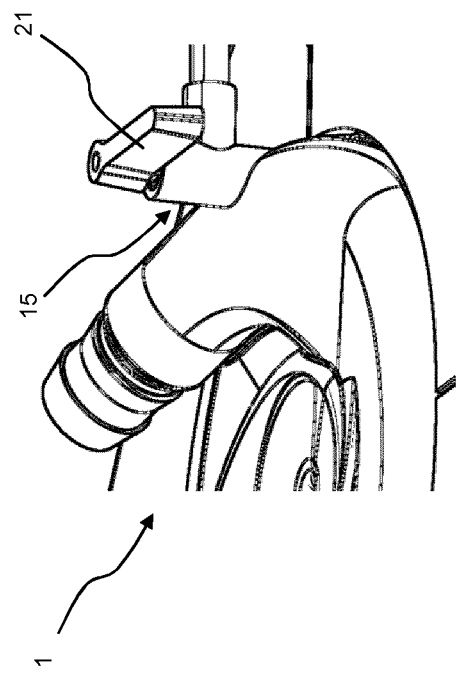
FIG. 8: an enlarged illustration of a section illustrated in FIG. 7, wherein the ventilation device is in a first operating condition.

FIG. 8 shows an enlarged illustration of a section shown in FIG. 7. The gas exchange unit 1 has an adjustment element 21 in the form of a rotating lever, by means of which the ventilation device 15 can optionally be transferred into a first operating condition or into a second operating condition. The ventilation device is in the first operating condition in the design shown in FIG. 8.

Figure 9:
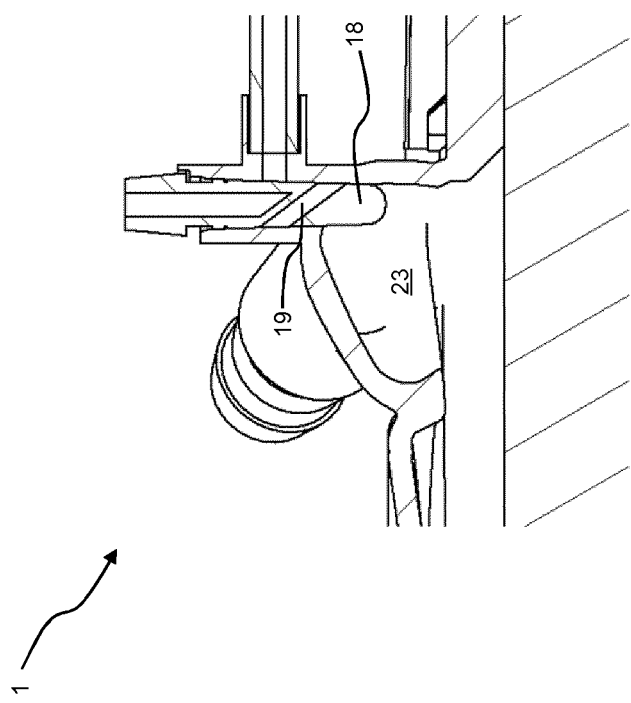
FIG. 9: a section view of the section shown in FIG. 8, FIG. 10: an enlarged illustration of a section illustrated in FIG. 7, wherein the ventilation device is in a second operating condition.

FIG. 9 shows a section illustration of the section illustrated in FIG. 8. As is clear from FIG. 9 the ventilation device 15 has a closure piston 18, which is connected with the adjustment element 21 in a torque-proof way. A fluid line 19 is located in the closure piston 18. In a first position of the closure element 18 illustrated in FIG. 8 the fluid line 19 is oriented in such a way that the fluid line 19 is not in fluid connection with the line 22. A flushing of the ventilation device is not possible with this design.

Figure 10:
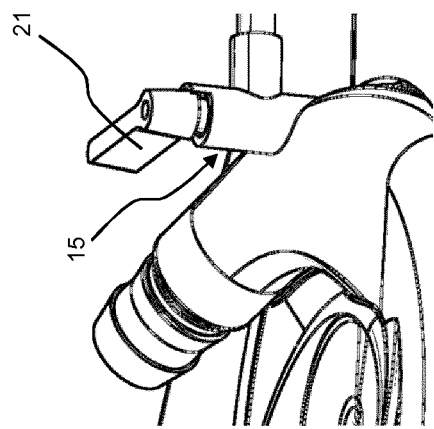

FIG. 10 also shows an enlarged illustration of a section shown in FIG. 7. With the design illustrated in FIG. 10 the adjustment element 21 has been rotated, so that the ventilation device 15 is in the second operating condition.

Figure 11:
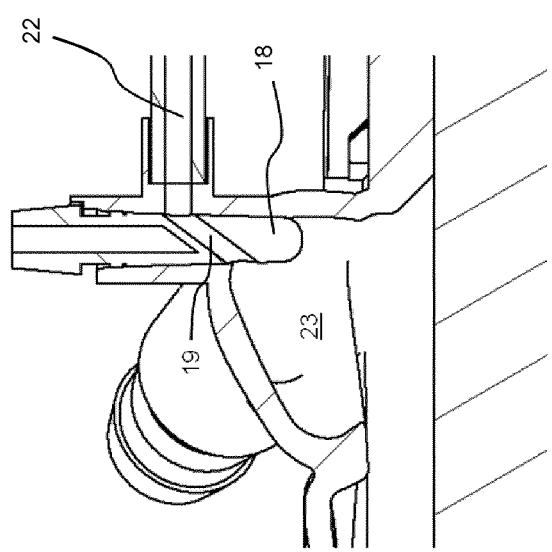
FIG. 11: a section illustration of the section shown in FIG. 10, FIG. 12: a perspective illustration of a ventilation device according to a third design.

FIG. 11 shows a section drawing of the section shown in FIG. 10. With the second operating condition of the ventilation device 15 the closure piston 18 is arranged in a second position, where the fluid line 19 is in fluid connection with the cavity 23 of the gas exchange unit 1. In addition the cavity 23 is in fluid connection with the line 22, and thus with the underpressure source 16 illustrated in FIG. 7. With the second position of the closure piston 18 the air collected in the cavity 23 can be vented via fluid line 19 and the line 20.

Figure 12:
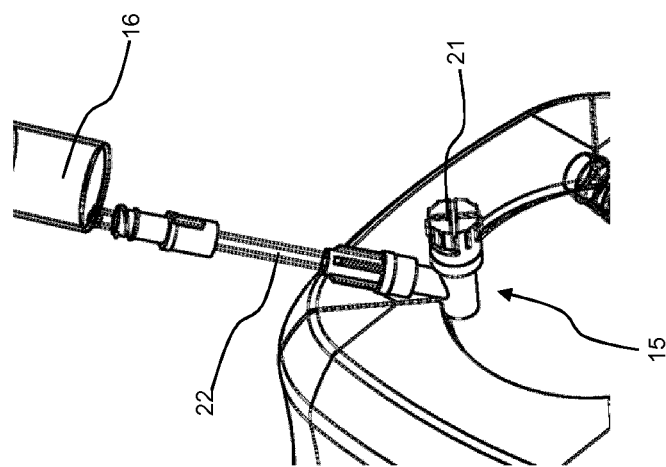

FIG. 12 shows a perspective illustration of a ventilation device according to a third design. The ventilation device 15 is in fluid connection with the underpressure source 16 via line 22. The design illustrated in FIG. 12 differs from the design illustrated in FIG. 7 here in the design of the adjustment element 21. It is clear from FIG. 13 that the adjustment element 21 is designed as a rotary knob.

Figure 14:
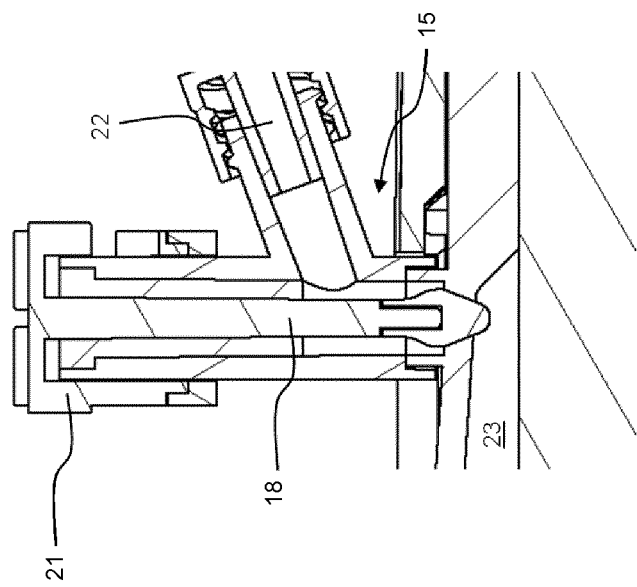
FIG. 14: a section illustration of the section shown in FIG. 13, FIG. 15: an enlarged illustration of a section illustrated in FIG. 12, wherein the ventilation device is in a second operating condition.
Figure 13:
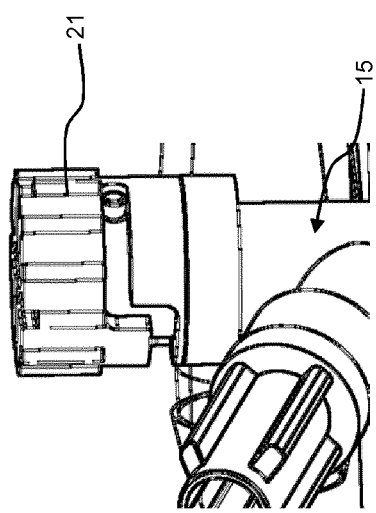
FIG. 13: an enlarged illustration of a section illustrated in FIG. 12, wherein the ventilation device is in a first operating condition.

FIG. 14 shows a section illustration of the ventilation device 15 shown in FIG. 13 and the adjustment element 21. As is clear from FIG. 14 no fluid connection exists between the line 22 and the cavity 23 in the first position of the adjustment element 18. Air located in the cavity 23 can therefore not be vented in the first position of the closure piston 18. The closure piston 18 is connected with the adjustment element 21 in a torque-proof way.

Figure 15:
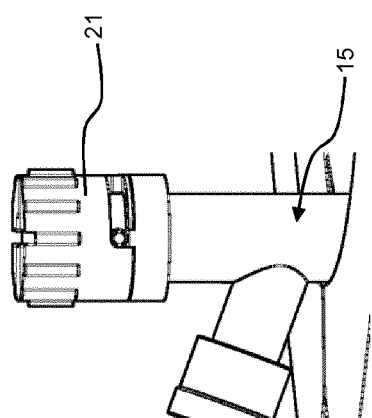

FIG. 15 shows an enlarged illustration of the ventilation device 15 shown in FIG. 12 and the adjustment element 21, wherein the ventilation device 15 is in the second operating condition. The adjustment element 21 is turned to transfer the ventilation device 15 from the first operating condition into the second operating condition.

Figure 16:
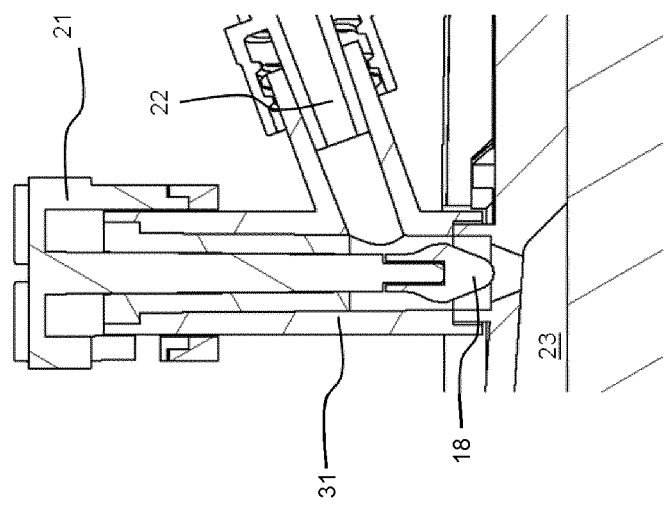
FIG. 16: a section illustration of the section shown in FIG. 15, FIG. 17: a section illustration of a ventilation device according to fourth design, where the ventilation device is in a first operating condition.

FIG. 16 shows a section illustration of the ventilation device 15 shown in FIG. 15 and the adjustment element 21. A fluid connection exists between the cavity 23 and the line 22 in the second position of the closure piston 18. The closure piston 18 is moved in a linear manner for transferring the closure piston 18 from the first position into the second position shown in FIG. 16. Air collected in cavity 23 can be vented to the underpressure source 16 through a gap between the closure piston 18 and a ventilation device casing 31 and via line 22.

Figure 17:
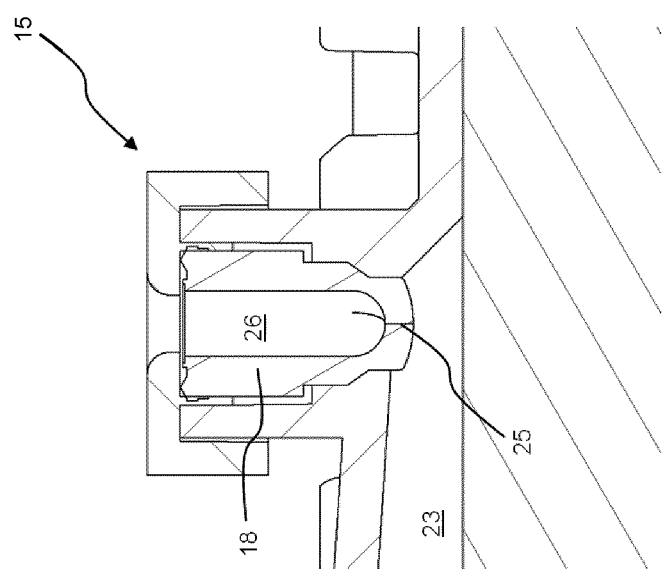

FIG. 17 shows a section illustration of the ventilation device according to a fourth design. The closure piston 18 of the ventilation device 15 differs from the closure piston described above in that it has a weak point 25. The weak point 25 equals a cut in the closure piston 18. The weak point 25 is arranged in an area of the closure piston 18 here, which extends into the cavity 23. A further difference consists of the closure piston 18 including a recess 26. In FIG. 17 the closure piston 18 is in the first position, so that air collected in the cavity 23 cannot be vented.

Figure 18:
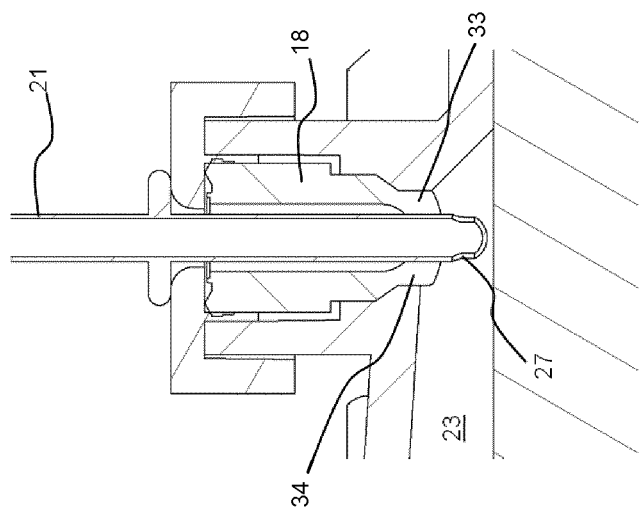
FIG. 18: a section illustration of the ventilation device according to the fourth design, where the ventilation device is in a second operating condition.

FIG. 18 shows a section illustration of the ventilation device 15 according to the fourth design, wherein the ventilation device 15 is in the second operating condition. As is clear from FIG. 18 the adjustment element 21 passes through the closure piston 18. In particular the adjustment element 21 passes through the same in the area of the weak point 25 of the closure piston 18. As a consequence of this passing of the adjustment element 21 through the closure piston 18 a piston section 33 and another piston section 34 move away from each other. The adjustment element 21 is partly arranged in the recess 26 here. The adjustment element 21 has an opening 27 in its section that lies in the cavity 23, via which air is vented from the cavity 23.

Figure 19:
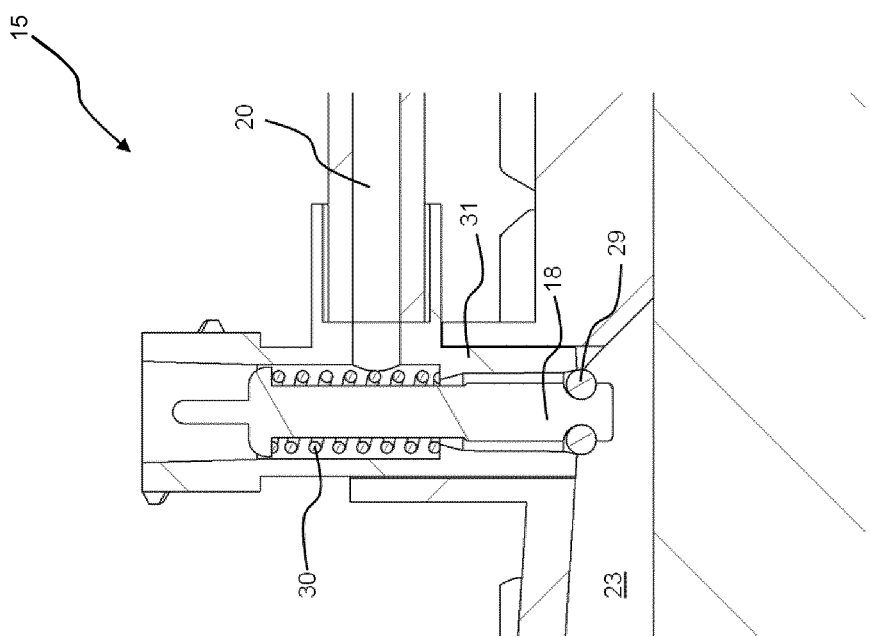
FIG. 19: a section illustration of a ventilation device according to a fifth design, where the ventilation device is in a first operating condition.

FIG. 19 shows a section illustration of the ventilation device 15 according to a fifth design. The ventilation device 15 has a sealing ring 29 fitted on the closure piston 18. In addition the ventilation device 15 has a return means 30 designed in such a way that it presses the closure piston 18 from the second position shown in FIG. 20 into the first position shown in FIG. 19. The return element 30 supports itself on the closure piston 18 at one end, and on a ventilation device casing 31 at the other end.

Figure 20:
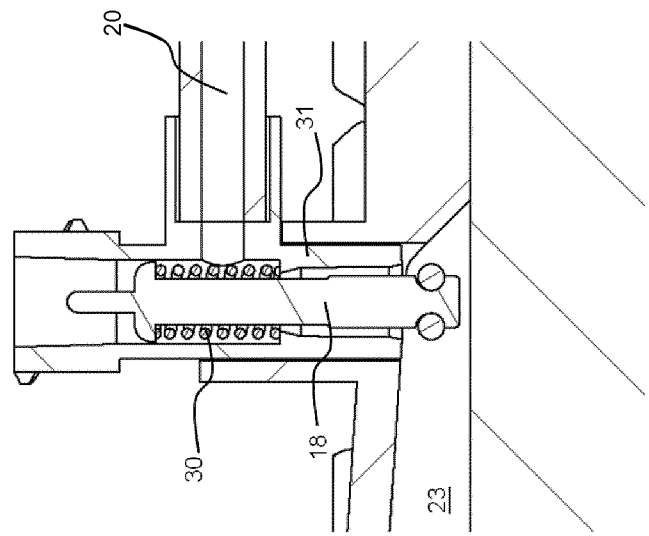
FIG. 20: a section illustration of a ventilation device according to the fifth design, where the ventilation device is in a second operating condition.

FIG. 20 shows a section illustration of the ventilation device 15 according to the fifth design, where the ventilation device 15 is in the second operating condition. As is clear from FIG. 20 the closure piston 18 is moved in a linear manner by an adjustment element 21 not shown here. The closure piston 18 is in particular pressed so far into the cavity 23 that a gap exists between the closure piston 18 and the ventilation device casing, through which air collected in the cavity 23 is vented. The air vented from the cavity flows through line 20 to the underpressure source 16. The return element 30 is tensioned when the closure piston 18 is transferred into the second position.

Figure 21:
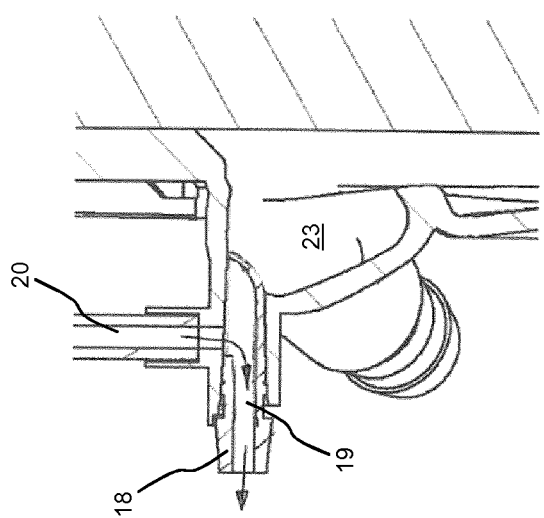
FIG. 21: a section illustration of a ventilation device according to a sixth design, where the ventilation device is in a first operating condition.

FIG. 21 shows a section illustration of a ventilation device 15 according to a sixth design, where the ventilation device 15 is in a first operating condition, where a flushing of the ventilation device 15 takes place. With the first position of the closure piston 18 shown in FIG. 21 the fluid line 19 of the closure piston 18 is in fluid connection with a supply line 20. A flushing agent is added via the supply line 20, which flows through the fluid line 19 as indicated by the arrows and exits via the closure piston 18. No fluid connection exists between the fluid line 19 and the cavity 23 in the first operating condition.

Figure 22:
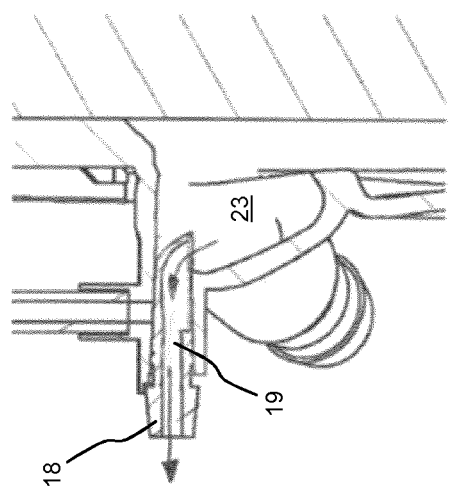
FIG. 22: a section illustration of a ventilation device according to a sixth design, where the ventilation device is in a second operating condition.

FIG. 22 shows a section illustration of a ventilation device 15 according to a sixth design, where the ventilation device 15 is in a second operating condition, where the ventilation process takes place. In the second position of the closure piston 18 a fluid connection exists between the fluid line 19 and the cavity 23. Air present in the cavity 23 can be vented via the fluid line 19 as shown by the arrows.

Figure 23:
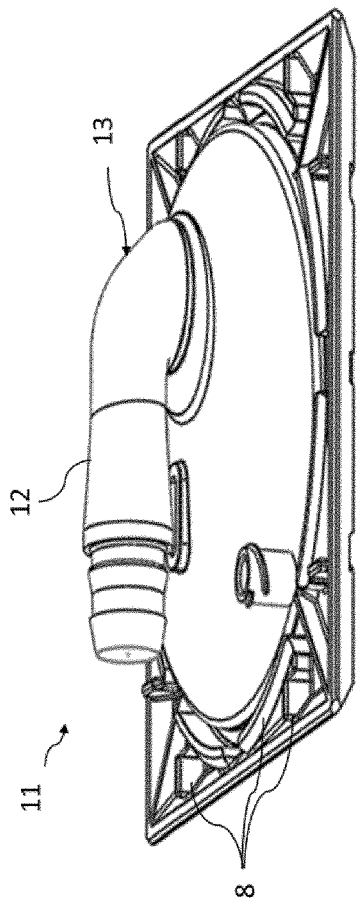
FIG. 23: an embodiment example of an outlet casing.

FIG. 23 shows an embodiment example of an outlet casing 11. The outlet casing 11 has an outlet 12. The cross-section surface of the outlet 12 reduces in flow direction as shown in the cross-section view of the outlet in FIG. 22. The inlet casing 5, the outlet casing 11 and casing part 3 form a casing of the gas exchange unit 1.

The outlet 12 has a deflection 13. The deflection angle is 90°, but can also lie between 70° and 90°. The continuous reduction of the cross-section surface of the outlet 12 accelerates the fluid (blood), so that the formation of secondary turbulence or flow separations are effectively counteracted.

The outlet casing 11 optionally has stabilisers 8, which can be designed as bridges or cross members. During potting, where high temperatures can be reached, the geometry of the outlet casing 11 is thus maintained and will not change substantially if temperatures change.

Figure 24:
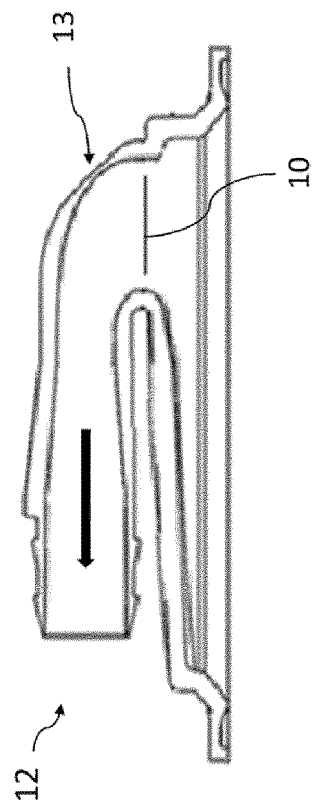
FIG. 24: a cross-section view of an outlet.

FIG. 24 shows a cross-section view of the outlet 12. The cross-section surface 10 of the outlet 12 narrows continuously in flow direction of the fluid (blood) in the area of the change in main flow direction (deflection 13). The flow direction is indicated by an arrow. The narrowing can be asymmetrical. The cross-section surface 10 can be variable along the length of the outlet 12. The fluid (blood) is accelerated by a continuous cross-section surface reduction on the outlet side of the gas exchange unit 1.

It should be noted that the methods, devices and systems described in this document can be used on their own as well as in combination with other methods, devices and systems described in this document. All aspects of the methods, devices and systems described in this document can also be combined with each other in many ways. In particular the characteristics of the claims can be combined with each other in many ways.

The invention has been described in detail with reference to the drawings and the above description. This invention can however be realised in many different forms and should not be interpreted as limited to the embodiments illustrated here, instead these embodiments are provided to make this disclosure thorough and complete, and do not exhaust the scope of protection of the invention to its full extent for a person skilled in the art. The terminology used in the detailed description of the embodiments illustrated in the enclosed drawings are not intended to limit the invention. Identical reference numbers in the drawings refer to identical elements.

The invention claimed is:

1. A gas exchange unit for enriching blood with oxygen and removing carbon dioxide from the blood, the gas exchange unit comprising:
   a plurality of hollow fiber mats;
   a casing comprising an inlet casing; and
   an inlet configured to receive blood, wherein the inlet is coupled to the inlet casing in an acentric position and wherein the inlet has a slanted orientation configured to cause the blood to flow in a rotational direction, and
   wherein the inlet casing comprises one or more surface structures which are coupled to an inner blood conveying surface of the inlet casing,
   wherein the one and more surface structures comprises vane-shaped structures of different sizes configured to cause a substantially homogeneous blood flow through inlet casing and configured to cause a consistent, homogeneous flow through the gas exchange unit for better enriching blood with oxygen and removing carbon dioxide from the blood.

2. The gas exchange unit according to claim 1, wherein the inlet is arranged on the casing of the gas exchange unit.

3. The gas exchange unit according to claim 1, wherein the one or more surface structures are arranged on the inner blood conveying surface of the inlet casing in a vane shape or bridge shape or as cross members.

4. The gas exchange unit according to claim 1, wherein the inlet has a cross-section surface that widens continuously in a flow direction.

5. The gas exchange unit according to claim 1, wherein a diameter widening of the inlet along a run length of the inlet is less than 45°.

6. The gas exchange unit according to claim 1, wherein the inlet has a cross-section surface that widens asymmetrically.

7. The gas exchange unit according to claim 1, wherein the inlet has a cross-section surface area that is variably widened and/or narrowed along a length of the inlet.

8. The gas exchange unit according to claim 1, wherein the gas exchange unit has an outlet, a cross-section surface of which reduces continuously in flow direction.

9. The gas exchange unit according to claim 1, wherein the gas exchange unit has an outlet that comprises a deflection.

10. The gas exchange unit according to claim 1, further comprising a ventilation device.

11. The gas exchange unit according to claim 10, characterised in that:
   a. the ventilation device is configured to be transferred into a first operating condition, where a flushing of the ventilation device can be realized, or into a second operating condition, where a ventilation of a cavity of the gas exchange unit can be realized, or that
   b. the ventilation device is configured to be transferred into a first operating condition, where no ventilation of a cavity of the gas exchange unit can be realized, or into a second operating condition, where a ventilation of the cavity of the gas exchange unit can be realized.

12. The gas exchange unit according to claim 10, wherein the ventilation device comprises a flexible membrane.

13. The gas exchange unit according to claim 10, characterized by an adjustment element for transferring the ventilation device into a first operating condition or into a second operating condition.

14. The gas exchange unit according to claim 10, characterized in that the ventilation device has a closure piston that can be transferred into a first position for realizing a first operating condition or into a second position for realizing a second operating condition.

15. The gas exchange unit according to claim 14, characterized in that the closure piston has a fluid line, which
   a. is not in fluid connection with a cavity in the first position and is in fluid connection in a second position and/or which
   b. is in fluid connection with a supply line for supplying a flushing agent in the first position and is not in fluid connection with the supply line in the second position.

16. The gas exchange unit according to claim 14, characterized in that the closure piston is
   a. mounted to be moved in a linear manner and/or
   b. rotatably mounted and/or
   c. is designed in such a way that a piston section can be moved relative to another piston section
   for transferring from the first position into the second position or vice versa.

17. The gas exchange unit according to claim 14, characterized in that
   a. a sealing ring is fitted on the closure piston and/or that
   b. a return element is operatively connected with the closure piston in such a way that the return element presses the closure piston from the second position into the first position.

18. The gas exchange unit according to claim 14, characterized in that the closure piston has a weak point, designed in such a way that
   a. an adjustment element passes through the closure piston in the second position of the closure piston and/or
   b. ventilation cannot be realized in the first position of the closure piston.

19. The gas exchange unit according to claim 1, wherein the hollow fiber mats are embedded in the gas exchange unit and a transition from the embedded hollow fiber mats to adjacent components has slanting transitions.

20. The gas exchange unit according to claim 1, characterized in that the inlet casing has stabilizers.

21. The gas exchange unit according to claim 1, wherein the ventilation device is arranged centrally within the gas exchange unit.

22. The gas exchange unit according to claim 1, wherein the vane-shaped structures of different size are arranged one behind the other.

* * * * *